US00PP37760P2

(12) United States Plant Patent
Holtmaat

(10) Patent No.: US PP37,760 P2
(45) Date of Patent: Oct. 13, 2026

(54) ***RUDBECKIA* PLANT NAMED 'RUDBSU674'**

(50) Latin Name: *Rudbeckia hirla*
Varietal Denomination: RUDBSU674

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 19/463,090

(22) Filed: Jan. 29, 2026

(30) Foreign Application Priority Data

Oct. 27, 2025 (QZ) ..... PBR 20252211

(51) Int. Cl.
*A01H 5/02* (2018.01)
*A01H 6/14* (2018.01)

(52) U.S. Cl.
USPC ..... Plt./474
CPC ..... *A01H 6/14* (2018.05)

(58) Field of Classification Search
USPC ..... Plt./474
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Rudbeckia* plant named 'RUDBSU674' that is characterized by its short plant height, its floriferous blooming habit, its inflorescences with multi-colored ray florets that are yellow and very dark red towards the base, and its vigorous growth habit.

2 Drawing Sheets

Botanical classification: *Rudbeckia hirta.*
Variety denomination: 'RUDBSU674'.

CROSS-REFERENCE TO RELATED APPLICATIONS

This application claims priority to European Community Plant Variety Office (CPVO) Plant Breeder's Rights Application No. 2025/2211 filed on Oct. 27, 2025, under 35 U.S.C. 119(f), the entire contents of which is incorporated by reference herein. This application is co-pending with a U.S. Plant Patent Application filed for a plant derived from the same breeding program that is entitled *Rudbeckia* Plant Named 'RUDBKS772' (Co-pending U.S. application Ser. No. 19/463,084).

BACKGROUND OF THE INVENTION

The present invention relates to a new and distinct cultivar of *Rudbeckia hirta* and will hereafter by referred to by its cultivar name, 'RUDBSU674'. The new cultivar is an herbaceous perennial grown for use as a landscape plant.

'RUDBSU674' was selected in July of 2021 as a single unique plant by the Inventor from amongst seedlings in a trial field in Zuidwolde, Netherlands. The trial field had been planted with seed derived from open pollination of numerous unpatented and unnamed proprietary plants from the Inventor's breeding program. The collected seeds were pooled before sowing and therefore the parentage is unknown.

Asexual propagation of the new cultivar was first accomplished under the direction of the Inventor by tissue culture using meristematic tissue in Heerhugowaard, The Netherlands in May of 2025. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'RUDBSU674' as a unique cultivar of *Rudbeckia.*

1. 'RUDBSU674' exhibits a short plant height.
2. 'RUDBSU674' exhibits a floriferous blooming habit.
3. 'RUDBSU674' exhibits inflorescences with multi-colored ray florets that are yellow with the lower half very dark red towards the base.
4. 'RUDBSU674' exhibits a vigorous growth habit.

'RUDBSU674' can be compared to the *Rudbeckia* cultivars 'RUDLS291' (U.S. Plant Pat. No. 32,570) and 'RUDHT53' (U.S. Plant Pat. No. 30,727). 'RUDLS291' is similar to 'RUDBSU674' in having a short plant height and a floriferous blooming habit. 'RUDLS291' differs from 'RUDBSU674' in having smaller inflorescences, ray florets with the lower half yellow in color, and an earlier blooming season. 'RUDHT53' is similar to 'RUDBSU674' in having green foliage and a vigorous growth habit. 'RUDHT53' differs from 'RUDBSU674' in having a shorter plant height, smaller inflorescences, and ray florets that are solid yellow-orange in color.

'RUDBSU674' can also be compared to the co-pending cultivar *Rudbeckia hirta* 'RUDBKS772'. 'RUDBKS772' differs from 'RUDBSU674' in having ray florets that are yellow from the top to the mid-section and lighter red towards the base.

BRIEF DESCRIPTION OF THE DRAWINGS

The accompanying color photographs illustrate the overall appearance and distinct characteristics of the new *Rud-*

*beckia*. The photographs were taken of a 4-month-old plant of 'RUDBSU674' as grown outdoors in a 19-cm container in Zuidwolde, The Netherlands.

Figure 1:
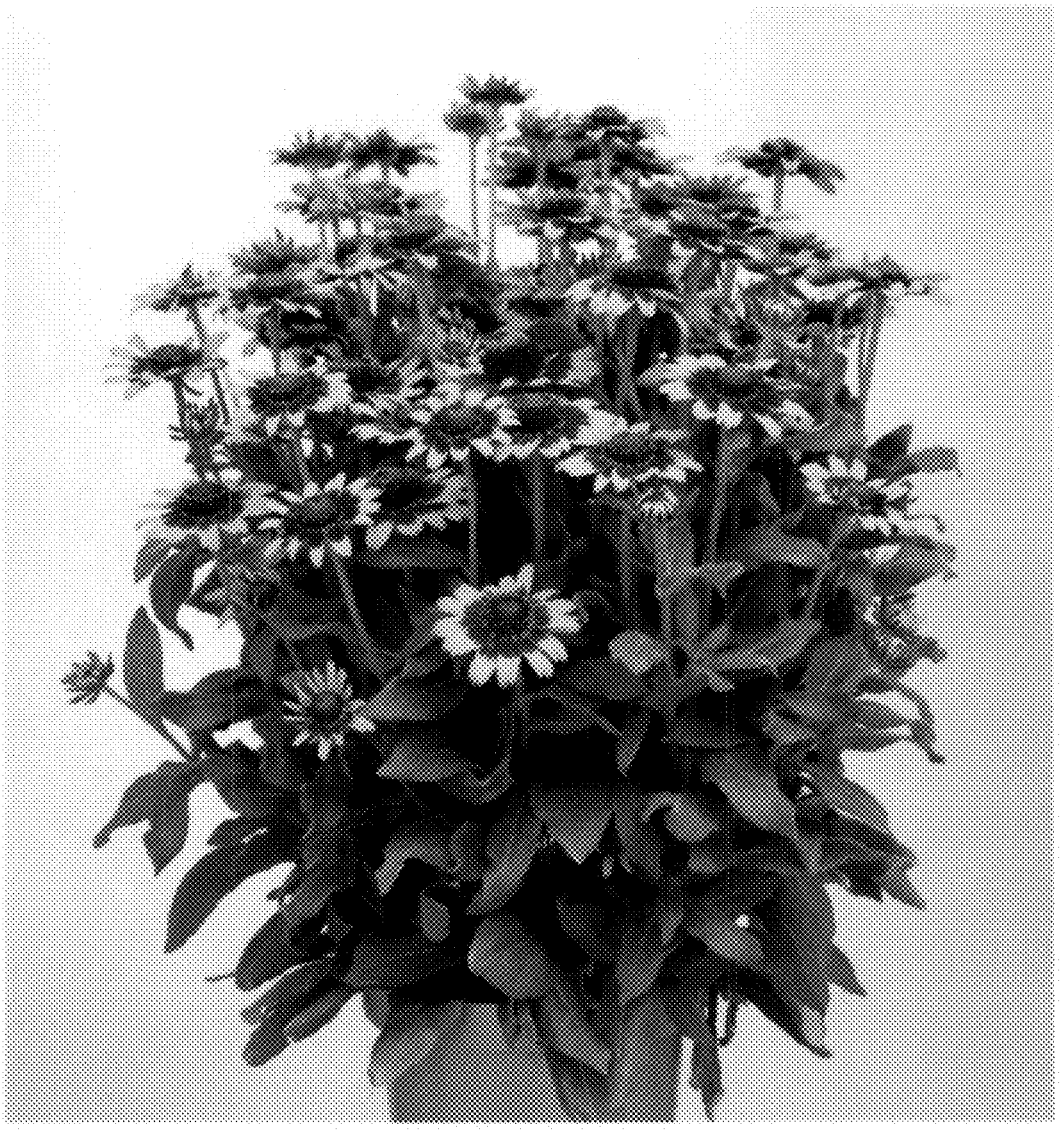

The photograph in FIG. 1 is a side view of 'RUDBSU674' in bloom.

Figure 2:
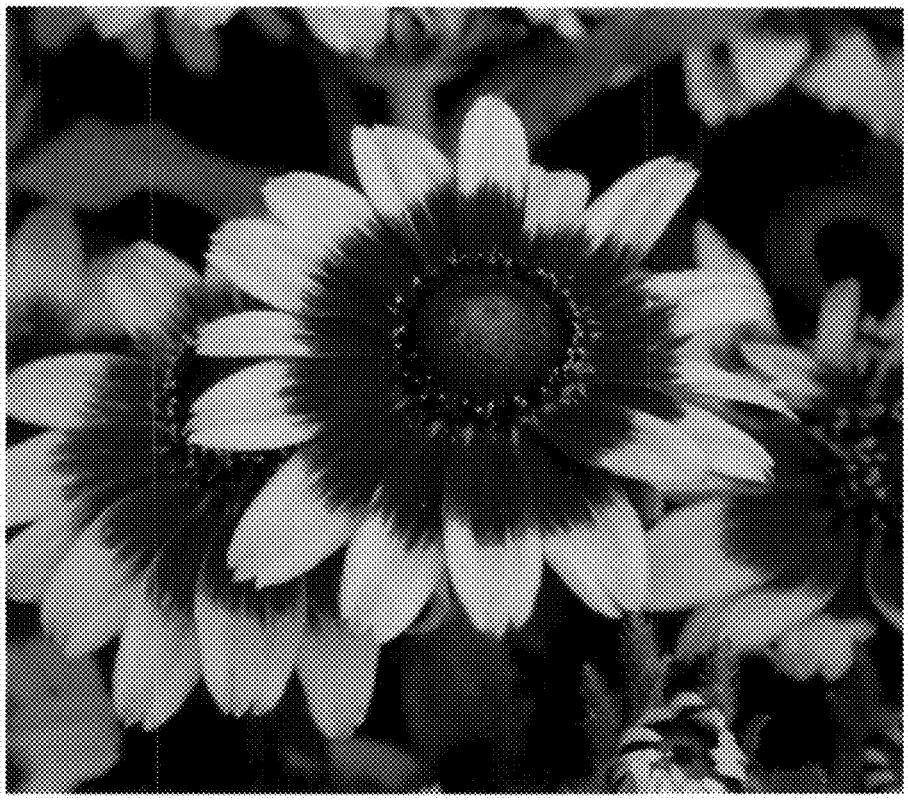

The photograph in FIG. 2 provides a close-up view of an inflorescence of 'RUDBSU674'.

Figure 3:
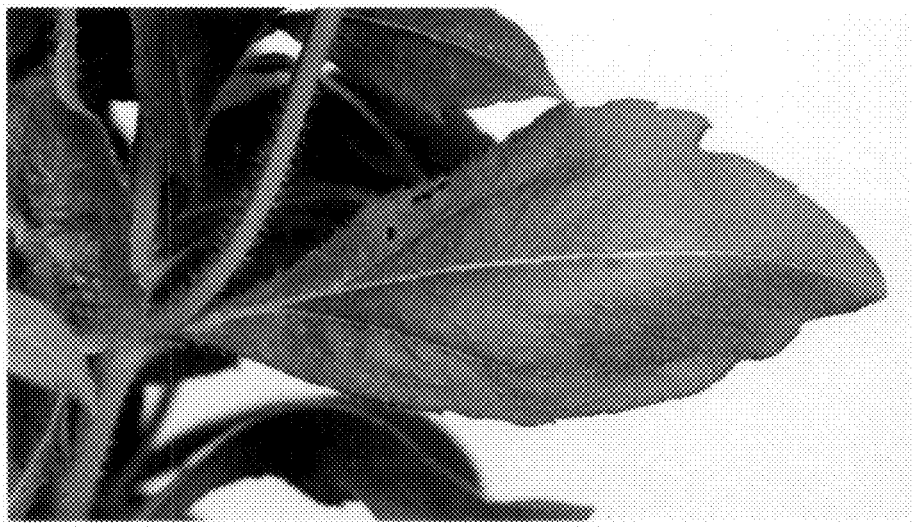

The photograph in FIG. 3 provides a close-up view of a leaf of 'RUDBSU674'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 4-month-old plants of 'RUDBSU674' as grown outdoors in 19-cm containers in Zuidwolde, The Netherlands. The phenotype of the new cultivar may vary with variations in environmental, climatic, and cultural conditions, as it has not been tested under all possible environmental conditions. The color determination is in accordance with the 6$^{th}$ edition 2015 Colour Chart of The Royal Horticultural Society, London, England (2019 reprint), except where general color terms of ordinary dictionary significance are used.

General description:

*Blooming period*.—Early summer to late summer in The Netherlands.

*Plant type*.—Biennial.

*Plant habit*.—Upright, compact.

*Plant shape*.—Broadly obovate.

*Height and spread*.—Average of 43.4 cm in height from soil level to top of foliar plane and 50 cm in height from soil level to top of floral plane, 52 cm in diameter as a 4-month-old plant as grown in a container.

*Cold hardiness*.—At least in U.S.D.A. Zone 4.

*Diseases and pests*.—No susceptibility or resistance to diseases or pests has been observed.

*Root description*.—Fine and fibrous.

*Propagation*.—Tissue culture.

*Root development*.—4 to 6 weeks for root initiation with a fully rooted plant produced in an average of 8 weeks.

*Growth rate and vigor*.—Moderate to highly vigorous, a finished plant is produced in an average of 4 months in a 13-cm container or larger.

Branch description:

*Shape*.—Moderately angled, 5-sided.

*Branch color*.—Young stems; 144A, mature stems; 144B, internodes; 144B.

*Branch size*.—An average of 5 mm in diameter and an average of 26.2 cm in length.

*Branch surface*.—Moderately glossy and densely covered with strigose hairs; an average of 2 mm in length and N155A in color.

*Branch number*.—Average of 8 main stems, 3 lateral branches per main stem.

*Internode length*.—An average of 2.7 cm in length.

*Branch aspect*.—Main stems; average of 30° to vertical, lateral branches; average of 20° to main stems.

*Branching*.—Freely branching from base with lateral stems.

Foliage description:

*Leaf shape*.—Elliptic-obovate to obovate, slightly convex.

*Leaf division*.—Simple.

*Leaf base*.—Long cuneate.

*Leaf apex*.—Rounded to broadly bluntly acute.

*Leaf venation*.—Pinnate, color; upper surface 148B, lower surface 144B.

*Leaf margins*.—Entire to coarsely very shallow serrate, non-undulate to coarsely slightly undulate.

*Leaf attachment*.—Petiolate.

*Leaf arrangement*.—Alternate.

*Leaf size*.—Average of 10.2 cm in length and 4.3 cm in width.

*Leaf color*.—Young upper surface; 137B, main vein 145D, young lower surface; 138B, main vein 142D, mature upper surface; NN137B, mature lower surface; 146B.

*Leaf surface*.—Both surfaces matte, very rough to the touch, densely pubescent with short strigose hairs; an average of 1 mm in length and N155A in color.

*Petioles*.—Average of 5 mm in length, flattened, average diameter at widest point 8 mm and at narrowest point 3 mm, upper surface color; N148D, lower surface color; 144C, both surfaces slightly glossy and densely covered with strigose hairs; an average of 2 mm in length and N155A in color.

Flower description:

*Type*.—Terminal capitulum, consisting of ray florets and disc florets.

*Capitulum number*.—Average of 4 per stem, 100 per plant.

*Lastingness of inflorescence*.—Average of 2 weeks, persistent.

*Capitulum size*.—Average of 2.2 cm in height, 6.7 cm in diameter, disc diameter 2.4 cm.

*Fragrance*.—None.

*Involucral bracts* (*phyllaries*).—Cuneate base, bluntly acute apex, narrow oblong in shape, margins revolute, average of 27 arranged in 2 rows, rotate, held in an average angle of 0° to horizontal, 2 cm in length and 6 mm in width, color; upper surface when fully open NN137B, lower surface when fully open 138A, upper surface is very slightly glossy, lower surface is matte, all surfaces including margins are moderately covered with strigose hairs; an average of 2 mm in length and N155A in color.

*Receptacle*.—Ovate in shape, an average of 9 mm in height, 6 mm in diameter, NN155D in color.

*Inflorescence buds*.—Shape; oval, immature ray florets pointed upward and slightly curled inwards, 2 cm in length, 1.4 cm in width, color; immature ray florets 11B, immature involucral bracts upper surface 146A, lower surface 146B, both surfaces are glossy, densely covered with strigose hairs, on immature ray florets hairs are adpressed, 1 mm in length, 11B in color, immature involucral bracts, 2 mm in length, NN155D in color.

*Peduncle*.—Strong, straight on top of main flowering stem, average of 9.4 cm in length and 4 mm in diameter, color; 144A, and 146A, surface moderately glossy and densely covered with short strigose hairs; an average of 2 mm in length and N155A in color.

*Ray florets.*—17 (ranging between 15 and 19), rotate around the disc in 1 row, oblong to narrow elliptic in shape, average of 5.8 cm in length and 2.3 cm in width, praemorse apex that is sometimes deeply emarginate, cuneate base, entire margins, both surfaces are glabrous and velvety, densely covered with very short hairs, 0.1 mm in length, matches surface color, held in an average angle of 2.5°, color; when opening upper surface 14A, top 12A, when opening lower surface 10B, top 55C, when fully open upper and lower surface 187A, top half and base 17B.

*Disc florets.*—Average of 1,000, 15 whorls arranged spirally on a conical receptacle, lower 90% fused into tube, tubular, upright, 9 mm in length and 3 mm in width, free lobes have entire margins, apices of free lobes acute and curled backwards, both surfaces glabrous, slightly glossy, color; when opening upper surface NN155D, top 187A, when opening lower surface lower ⅓$^{rd}$ NN155D, top ⅔$^{rd}$ 187A, when fully open upper and lower surface lower half NN155D, top half a blend of 187A and 203A, no spines, but a single bract is placed beside each disc floret; 1 per disc floret, flattened, an average of 7 mm in length and 1 mm in diameter, oblanceolate in shape, acute apex, narrowly cuneate base, color; apex 187B, mid-section 175C and NN155B, veins near margins 187B, matte surface and moderately pubescent on the apex with hairs; an average of 1 mm in length, 187B in color.

Reproductive organs (present on disc florets only):

*Gynoecium.*—Pistil; 1, 6 mm in length, style; 4.5 mm in length, color; NN155A, top 203B, stigma; cleft, decurrent, 6 mm in diameter, 203C in color, ovary; 160B in color.

*Androecium.*—Stamens; 5, filaments; 1 mm in length, NN155C in color, anthers; narrow oblong in shape, 3 mm in length, 0.5 mm in width, 199D in color, pollen; moderate in quantity, 14A in color.

*Fruit/seed.*—None observed to date.

It is claimed:

1. A new and distinct cultivar of *Rudbeckia* plant named 'RUDBSU674' substantially as herein illustrated and described.

* * * * *